(12) United States Patent
Sugiya et al.

(10) Patent No.: US 6,603,032 B1
(45) Date of Patent: Aug. 5, 2003

(54) 1,2-BIS(METHYL(1,1,3,3-TETRAMETHYLBUTYL)-PHOSPHINO) ETHANE, PROCESS THE PREPARATION THEREOF, TRANSITION METAL COMPLEXES CONTAINING THE SAME AS A LIGAND AND USES THEREOF

(75) Inventors: Masashi Sugiya, Tokyo (JP); Hiroyuki Nohira, Saitama (JP)

(73) Assignee: Nippon Chemical Industries Co., Ltd., Tokyo (JP)

( * ) Notice: Subject to any disclaimer, the term of this patent is extended or adjusted under 35 U.S.C. 154(b) by 0 days.

(21) Appl. No.: 10/148,895
(22) PCT Filed: Dec. 20, 1999
(86) PCT No.: PCT/JP99/07156
§ 371 (c)(1), (2), (4) Date: Jun. 18, 2002
(87) PCT Pub. No.: WO01/46098
PCT Pub. Date: Jun. 28, 2001

(51) Int. Cl.[7] .................................................. C07F 9/50
(52) U.S. Cl. ............................ 556/18; 568/8; 205/420
(58) Field of Search ............................ 568/8; 205/420; 556/13, 18; 560/8, 19, 129; 562/400, 405

(56) References Cited

U.S. PATENT DOCUMENTS 3,518,312 A * 6/1970 Maier ............................ 568/8
5,723,642 A * 3/1998 Sturmer et al. ............... 556/18
5,872,279 A * 2/1999 Sugiya et al. ................. 562/8
6,214,196 B1 * 4/2001 Sugiya et al. ............... 205/416

FOREIGN PATENT DOCUMENTS

JP 11080179 * 3/1999

* cited by examiner

Primary Examiner—Jean F. Vollano
(74) Attorney, Agent, or Firm—Armstrong, Westerman & Hattori, LLP

(57) ABSTRACT

The present invention provides a novel bisphosphine compound having a chiral center on the phosphorus atom, which is suitable as a ligand for an asymmetric catalyst for use in asymmetric hydrogenation, this bisphosphine compound being represented by the following formula (1):

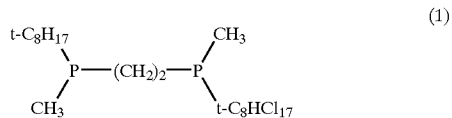

(where t—$C_8H_{17}$ denotes 1,1,3,3-tetramethylbutyl), and a process for the production of this bisphosphine compound. Also provided are a transition metal complex having this bisphosphine compound as a ligand, and a process for the asymmetric hydrogenation of an unsubstituted carboxylic acid or its ester.

7 Claims, No Drawings

1,2-BIS(METHYL(1,1,3,3-TETRAMETHYLBUTYL)-PHOSPHINO) ETHANE, PROCESS THE PREPARATION THEREOF, TRANSITION METAL COMPLEXES CONTAINING THE SAME AS A LIGAND AND USES THEREOF

This application is a 371 of PCT/JP99/07156 filed Dec. 12, 1999, now WO 01/46098.

TECHNICAL FIELD

The present invention relates to a novel bisphosphine compound having a chiral center on the phosphorus atom, which is useful as a ligand for asymmetric catalysts for use in asymmetric hydrogenation, and a process for the production of this bisphosphine compound, and further to a transition metal complex having this bisphosphine compound as a ligand, and a process for the asymmetric hydrogenation of an unsaturated carboxylic acid and its ester using this transition metal complex as an asymmetric catalyst for asymmetric hydrogenation.

BACKGROUND ART

Asymmetric catalytic synthesis is of great importance as the method for producing optically active fine chemicals that include agricultural products, pharmaceutical preparations and so on. An optically active phosphine ligand has played a major role as the ligand for transition metal complexes, and hence, a wide variety of related ligands have been reported to date. They are disclosed, for instance, in "Asymmetric Synthesis", Vol. 5, authored by J. D. Morrison (published in 1985 by Academic Press Inc.), "Fundamentals and Applications of Chiral Technology" authored by Kazuo Achinami (published in 1999 by IBC) and "Asymmetric Catalysis in Organic Synthesis" authored by Ryoji Noyori.

Heretofore, compounds capable of causing a substituent such as a phenyl group existing on the phosphorus atom to be nonequivalent by C-chirality or axial asymmetry have been positively studied because they are obtainable by simple synthesis. It has been reported, however, that phosphine compounds having a chiral center directly on the phosphorus atom exert the most outstanding capability to develop asymmetry. Of these ligands, 1,2-bis(o-methoxyphenyl)phenylphosphino)ethane (generally called DIPAMP) is known which is a ligand having been studied in the earliest stage (U.S. Pat. No. 4,008,281 and Japanese Unexamined Patent Application Publication No. 50-113489). Furthermore, a new bisphosphine ligand structured to have a 1,2-bis(phosphino)-ethane group has been proposed by Imamoto et al. (J. Am. Chem. Soc., 1998, 120, pp. 1635–1636 and Japanese Unexamined Patent Application Publication No. 11-80179).

Thus, the 1,2-bis(phosphino)ethane-structured bisphosphine is known to be important as a chiral ligand. For an asymmetric reaction to progress with high reactivity, a substituent-containing aromatic group or a bulky alkyl group needs to be essentially existent on the chiral center, i.e., on the phosphorus atom. The bulky alkyl group known to be possibly attached to the P atom of such a 1,2-bis(phosphine) ethane structure, however, is limited only to a lower alkyl group such as 1,1-diethylpropyl or t-butyl, and a cycloalkyl group such as cyclopentyl, cyclohexyl or 1-adamantyl. Also in the case of other bisphosphine ligands, it is art-recognized that as the bulky alkyl group to be attached to the chiral center, that is, to the phosphorus atom, a chain alkyl group is usually used which has 2 to 4 carbon atoms and is typified by a t-butyl group and that as the alkyl group having a much larger number of carbon atoms, a cycloalkyl group is usually used which is typified by a cyclopentyl or cyclohexyl group. With regard to the chain alkyl group, a bulky alkyl group having 8 or more carbon atoms stands wholly unknown. Therefore, the 1,1,3,3-tetramethylbutyl group-containing bisphosphine compound according to the present invention can be said to be absolutely novel as far as the present inventors know.

The method disclosed in Japanese Unexamined Patent Application Publication No. 11-80179 involves stereoselective deprotonation of (−)-sparteine in an equimolar amount with S-butyllithium at a cryogenic temperature of −78° C., thereby obtaining an optically active bisphosphine-borane complex. Such a cryogenic temperature, however, is generally extremely difficult to carry out industrially and hence is far from being practically applicable. In addition, the S-butyllithium is a compound that is vigorously active with respect to oxygen and moisture in the air and is difficult to handle on an industrial scale. As a further problem, an optically active form that can be obtained is limited only to a (S, S) form as an absolute configuration, and therefore, this is less advantageous to industrialization.

Optically active bisphosphine ligands have been thus far developed as mentioned above, but they cannot be said to be sufficient in respect of selectivity, catalytic activity and so on. Providing a phosphine ligand not yet known is crucial when the substrates, asymmetry conditions and the like are considered.

To settle the above-noted problems, the present inventors have conducted extensive research, finding that a transition metal complex having a novel 1,1,3,3-tetramethylbutyl group-containing bisphosphine compound as a ligand exhibits a high asymmetric catalytic activity, which group is a bulky substituent having 8 carbon atoms and represented by the foregoing general formula (1), and can also give both (S, S) and (R, R) forms as absolute configurations. This finding has led to completion of the present invention.

Namely, the objects of the invention are to provide a novel bisphosphine compound that is useful as a ligand capable of yielding a higher asymmetric catalytic activity than conventional catalysts, a process for producing the above bisphosphine compound, a transition metal complex having as a ligand the above bisphosphine compound capable of yielding a higher asymmetric catalytic activity than conventional catalysts, and a process for asymmetrically hydrogenating an unsaturated carboxylic acid and its ester using the above transition metal complex as a catalyst.

Disclosure of the Invention

The novel bisphosphine compound intended to be provided by the present invention is a 1,2-bis(methyl(1,1,3,3-tetramethylbutyl)-phosphino)ethane represented by the following general formula (1):

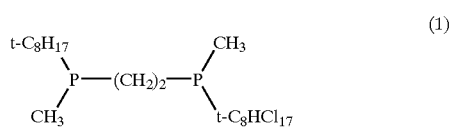

(where t—$C_8H_{17}$ denotes 1,1,3,3-tetramethylbutyl).

Moreover, the process for producing the above-mentioned bisphosphine compound comprises the steps of subjecting a phosphine oxide carboxylate represented by the following general formula (2):

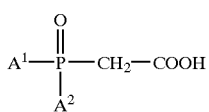

(2)

(where $A^1$ and $A^2$ denote a methyl group and a 1,1,3,3-tetramethyl-butyl group, respectively, and $A^1$ and $A^2$ denote their respective different groups) to Kolbe's electrolytic coupling reaction, thereby obtaining 1,2-bis(methyl(1,1,3,3-tetramethylbutyl)phosphinoyl)-ethane represented by the following general formula (3):

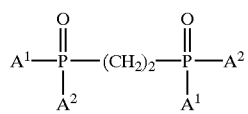

(3)

(where $A^1$ and $A^2$ have the same meanings as defined above, and $A^1$ and $A^2$ denote their respective different groups), and then reducing the resultant 1,2-bis(methyl(1,1,3,3-tetramethylbutyl)phosphinoyl)-ethane with a reducing agent.

Furthermore, the use of the above-mentioned bisphosphine compound is implemented in such a manner that a transition metal complex composed of the bisphosphine compound as a ligand is used as a catalyst to asymmetrically hydrogenate an unsaturated carboxylic acid and its ester.

Best Mode for Carrying Out the Invention

The present invention will now be described in detail.

In the 1,2-bis(methyl(1,1,3,3-tetramethylbutyl) phosphino)-ethane of the invention represented by the foregoing general formula (1), a racemic form and an optically active form are included. As the optically active form, (S, S), (R, R) and meso forms exist, but the invention embraces all such forms.

Next, the process is described for the production of the optically active 1,2-bis(methyl(1,1,3,3-tetramethylbutyl)-phosphino)ethane of the invention represented by the foregoing general formula (1).

The 1,2-bis(methyl(1,1,3,3-tetramethylbutyl)phosphino)-ethane of the invention represented by the foregoing general formula (1) can be easily produced, in essence, by performing a first step in which a phosphine oxide carboxylate represented by the foregoing general formula (2) is subjected to Kolbe's electrolytic coupling reaction, whereby 1,2-bis(methyl-(1,1,3,3-tetramethyl-butyl)phosphinoyl) ethane represented by the foregoing general formula (3) is obtained, and then a first step in which the resultant 1,2-bis (methyl(1,1,3,3-tetramethylbutyl)phosphinoyl)-ethane is reduced with a reducing agent.

<First Step>

The first step permits a phosphine oxide carboxylate of the foregoing general formula (2) to undergo Kolbe's electrolytic coupling reaction, thereby obtaining 1,2-bis(methyl (1,1,3,3-tetra-methylbutyl)phosphinoyl)ethane of the foregoing general formula (3).

In the foregoing general formula (2) representing the reactant material, i.e., the phosphine oxide carboxylate, $A^1$ and $A^2$ denote a methyl group and a 1,1,3,3-tetramethylbutyl group, respectively, and $A^1$ and $A^2$ denote their respective different groups.

Kolbe' electrolytic coupling reaction can be effected in accordance with the method previously proposed by the present inventors in Japanese Unexamined Patent Application Publication No. 11-228586. Specifically, this reaction employs a solvent in accomplishing electrolysis, which solvent includes methanol and hydrous methanol. When the hydrous methanol is used, the water content is preferably not more than 4%. Aqueous solution or aprotic polar solvent such as acetonitrile is not very desirable since the starting material is likely to give a by-product derived abnormally by Kolbe's reaction, such as olefin or alcohol (Hofer-Moest Reaction).

The pH of the electrolytic liquid is preferably neutral or acidulous. A support salt may be added, where desired, in stabilizing power distribution. Suitable support salts include sodium salts such as sodium perchlorate, sodium methylate and so on, and lithium salts such as lithium perchlorate and so on. Desirably, however, the use of a support salt should be avoided because the yield of the intended bisphosphine oxide decreases with increases in the amount of the salt. If such a support salt is anyway used, the amount of the salt to be added is preferably below 5 wt % based on 1 part by weight of the starting material.

As the electrode to be used, a platinum electrode is preferred to increase the concentration of radicals to be generated per unit area so that electrolysis can be effected at a high current density (at a high potential). An electrode made by plating platinum on a titanium plate can also be employed on an industrial scale. An electrode made of iridium, gold, palladium, lead dioxide or the like may be used in place of the platinum electrode. Preferably, the electrolytic liquid is maintained at a constant temperature by being immersed in a water bath. This is because the liquid temperature rises as the electrolysis volume increases. The electrolysis temperature is preferably relatively low, and the range of 0 to 20° C. is particularly desirable. Moreover, the electrolytic liquid is preferably stirred to maintain its temperature uniform.

The electrolysis is performed usually by constant-current, electrolysis, and the current capacity is in the range of 0.1 to 3 A, preferably 0.5 to 2 A. The electrode-to-electrode distance is usually in the range of about 1 to 5 mm to ensure that the current density be in the range of 10 to 100 mA/cm². The current distribution time is variable with the starting material and electrolysis conditions used, but is usually in the range of 0.5 to 36 hours, preferably about 1 to 10 hours.

Upon completion of the reaction, the solvent is removed by distillation to give a 1,2-bis(methyl(1,1,3,3-tetramethylbutyl)-phosphinoyl)ethane represented by the foregoing general formula (3). In the present invention, the resultant compound can be purified by conventional means such as recrystallization and so on.

According to the present invention, an optically active form of the 1,2-bis(methyl(1,1,3,3-tetramethybutyl) phosphino)-ethane of the foregoing general formula (1) can be easily produced, with axial asymmetry held on the P atom, by subjecting a reactant material, i.e., a phosphine oxide carboxylate of the foregoing general formula (2), to Kolbe's electrolytic coupling reaction stated earlier, wherein the reactant material has been optically resolved in advance, and subsequently by carrying out a second step that will be described later.

No particular restriction is imposed on the method for the optical resolution of the phosphine oxide carboxylate of the foregoing general formula (2). As one example, a method proposed previously by the present inventors is suitably useful in which a racemic mixture of the phosphine oxide carboxylate of the foregoing general formula (2) is treated with an optically active amine such as 1-phenylethylamine to form a diastereoisomer salt which is then resolved by utilizing the solubility difference with respect to a solvent used (Japanese Unexamined Patent Application Publication No. 10-29803).

<Second Step>

The second step permits the 1,2-bis(methyl(1,1,3,3-tetramethylbutyl)phosphinoyl)ethane of the foregoing general formula (3), which has been obtained as mentioned above, to be reduced with a reducing agent, thereby obtaining the intended 1,2-bis(methyl-(1,1,3,3-tetramethylbutyl)phosphino)ethane of the foregoing general formula (1).

The reducing agent for use in reducing the 1,2-bis (methyl-(1,1,3,3-tetramethylbutyl)phosphinoyl)ethane of the foregoing general formula (3) is not particularly restricted, but a silane compound may be generally employed. The silane compound includes, for example, trichlorosilane, dichlorosilane, methyl-dichlorosilane, dimethylchlorosilane, phenyldichlorosilane, phenylmethylchloro-silane, diphenylchlorosilane, phenylsilane and so on. Of these compounds, phenylsilane is preferred.

The amount of the reducing agent to be added is usually in the range of 1 to 100 mol, preferably 5 to 50 mol, based on 1 mol of the 1,2-bis(methyl(1,1,3,3-tetramethylbutyl)phosphinoyl)ethane of the foregoing general formula (3). The reaction temperature is usually in the range of room temperature to 150° C., preferably 50 to 120° C., whereas the reaction time is usually in the range of 1 to 48, preferably 5 to 24 hours.

In this way, the 1,2-bis(methyl(1,1,3,3-tetramethylbutyl)-phosphino)ethane of the foregoing general formula (1) is obtained in a racemic or optically active form. The optically active form depends on the (S) and (R) forms of the starting material, i.e., the phosphine oxide carboxylate of the foregoing general formula (2). When the above-described first and second steps are carried out using a desired form of starting material, the 1,2-bis(methyl-(1,1,3,3-tetramethylbutyl)phosphino)ethane of the foregoing general formula (1) can be synthesized in an optically active form chosen arbitrarily from (S, S), (R, R) and meso forms.

The 1,2-bis(methyl(1,1,3,3-tetramethylbutyl)phosphino)-ethane of the foregoing general formula (1) according to the present invention can cooperate as a ligand with a transition metal in forming the corresponding complex. The transition metal that can form a complex includes, for example, rhodium, ruthenium, iridium, palladium, nickel and so on. A rhodium metal is preferable.

In the formulae of transition metal complexes that will follow, cod denotes 1,5-cyclooctadiene, nbd denotes norbornadiene, Ph denotes phenyl, and Ac denotes acetyl, respectively, while L denotes the optically active 1,2-bis (methyl(1,1,3,3-tetramethyl-butyl)phosphino)ethane of the foregoing general formula (1).

<Rhodium Complex>

As the method of forming a complex using a rhodium metal together with the optically active 1,2-bis(methyl(1,1,3,3-tetra-methylbutyl)phosphino)ethane of the foregoing general formula (1) as a ligand, the optically active 1,2-bis (methyl(1,1,3,3-tetramethyl-butyl)-phosphino)ethane of the foregoing general formula (1) according to the present invention may be reacted, for example, with a bis-(cycloocta-1,5-diene)rhodium (I) tetrafluoroborate salt by a method disclosed, for example, in Courses in Experimental Chemistry, 4th Edition (edited by the Chemical Society of Japan, published by Maruzen Co., Ltd., Vol. 18, pp. 327–353).

Specific examples of the resulting compounds are enumerated below.

Rh(CO)(acac)(L), [Rh(cod)(L)]ClO$_4$, [Rh(cod)(L)]PF$_6$, [Rh(cod)-(L)]BF$_4$, [Rh(nbd)(L)]ClP$_4$, [Rh(nbd)(L)]PF$_6$, [Rh(nbd)(L)]BF$_4$, Rh(cod)(L)Cl, Rh(nbd)(L)Cl, Rh(cod)(L)Br and Rh(nbd)(L)Br.

<Palladium Complex>

A palladium complex can be prepared by a method disclosed by Uozumi and Hayashi (Y. Uozumi and T. Hayashi, J. Am. Chem. Soc., 1991, 113, 9887), wherein L is reacted, for example, with π-allylpalladium chloride. Specific examples of the resulting compound are enumerated below.

PdCl$_2$(L), (π-allyl)Pd(L), [Pd(L)]ClO$_4$, [Pd(L)]PF$_6$ and [Pd(L)]BF$_4$.

<Ruthenium Complex>

A ruthenium complex can be prepared by a method disclosed by Mashima et al. (K. Mashima, K. Kusano, T. Ohta, R. Noyori and H. Takaya, J. Chem. Soc., Chem. Commun., 1208 (1989)), wherein L and, for example, [Ru (p-cymene)I$_2$]$_2$ are stirred with heating in methylene chloride and ethanol. Specific examples of the resulting compounds are enumerated below.

[RuCl(benzene)(L)]Cl, [RuBr(benzene(L)]Br, [RuI (benzene)-(L)]I, [RuCl(p-cymene)(L)]Cl, [RuBr(p-cymene)(L)]Br, [RuI(p-cymene)(L)]I, [RuCl (mesitylene)(L)]Cl, [RuBr(mesitylene)(L)]Br, [RuI (mesitylene)(L)]I, [RuCl(hexamethylbenzene)(L)]Cl, [RuBr(hexamethylbenzene)(L)]Br and [RuL (hexamethylbenzene)-(L)]I.

<Iridium Complex>

An iridium complex can be prepared by a method disclosed by Mashima et al. (K. Mashima, T. Akutagawa, X. Zhang, T. Taketomi and H. Kumobayashi, J. Organomet. Chem., 1992, 428, 213), wherein L is reacted, for example, with [Ir(cod)(CH$_3$CN)$_2$]BF$_4$ with stirring in tetrahydrofuran. Specific examples of the resulting compounds are enumerated below.

[Ir(cod)(L)]ClO$_4$, [Ir(cod)(L)]PF$_6$, [Ir(cod)(L)]BF$_4$, [Ir (nbd)-(L)]ClO$_4$, [Ir(nbd)(L)]PF$_6$, [Ir(nbd)(L)]BF$_4$, Ir(cod)(L)Cl, Ir(nbd)(L)Cl, Ir(cod)(L)Br and Ir(nbd)(L) Br.

The transition metal complex, preferably the rhodium metal complex, derived from the optically active 1,2-bis (methyl(1,1,3,3-tetramethylbutyl)phosphino)ethane of the foregoing general formula (1) according to the present invention and a transition metal compound can be utilized as a catalyst for asymmetric synthesis.

Next, asymmetric hydrogenation is described which uses the transition metal complex of the present invention.

An unsaturated carboxylic acid of the following general formula (4):

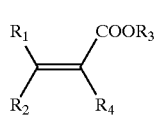

(4)

or its ester is asymmetrically hydrogenated using the transition metal complex of the invention as a catalyst, whereby a saturated carboxylic acid of the following general formula (5):

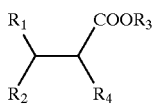

or its ester is obtained. The step for doing so can be performed in a conventional fashion. Namely, the unsaturated carboxylic acid of the foregoing general formula (4) or its ester is placed, together with the transition metal complex catalyst of the invention, in a pressure tight case under a nitrogen atmosphere, and reaction is effected with hydrogen gas filled.

In the foregoing general formulas (4) and (5), $R^1$, $R^2$ and $R^3$ denote a hydrogen atom, a straight- or branched-alkyl, aryl or aralkyl group, and $R^4$ denotes a straight- or branched-alkyl, aryl, aralkyl, —$CH_2COOR^5$ group (where $R^5$ denotes a straight- or branched-alkyl, aryl or aralkyl group) or —$NHR^6$ group (where $R^6$ denotes a formyl, straight- or branched-alkyl, aryl or aralkyl group).

Examples of the alkyl group defined in $R^1$ to $R^6$ are methyl, ethyl, propyl, isopropyl, butyl, octyl, decyl, and so on of C1 to C10. Examples of the aryl group are phenyl, naphthyl and so on of C6 to C12, and examples of the aralkyl group are benzyl, phenethyl, naphtylmethyl and so on. The alkyl, aryl, and aralkyl groups noted here may have substituents, which are inert to hydrogenation, such as alkyl, halogen, alkoxy and ester.

The amount of the transition metal complex of the present invention to be used as a catalyst is usually in the range of 0.02 to 0.00001 mol, preferably 0.005 to 0.0001 mol, based on 1 mol of the carboxylic acid of the foregoing general formula (4) or its ester. The solvent is not particularly restricted on condition that it is inert to the reactant material used and reaction product obtained. For example, alcohols, such as methanol, ethanol, isopropyl alcohol and the like, THF, benzene, toluene and so on can be used alone or as a mixed solvent. The amount of the solvent to be used is usually in the range of 0.5 to 200 mol, preferably 5 to 100 mol, based on 1 mol of the unsaturated carboxylic acid of the foregoing general formula (3) or its ester. The hydrogen gas pressure can be in the range of 0.1 to 100 atm, but is preferably in the range of 0.1 to 5 atm. This is because as the gas pressure becomes higher, asymmetric hydrogenation generally tends to be less selective, eventually causing a decline in asymmetry yield. The reaction temperature is in the range of 0 to 100° C., preferably 20 to 50° C.

With regard to the absolute configuration of the optically active 1,2-bis(methyl(1,1,3,3-tetramethylbutyl)phosphino) ethane of the foregoing general formula (1) according to the present invention, both forms of (R, R) and (S, S) are achieved. Hence, a specific target having a desired absolute configuration can be obtained with high optical purity and also with good yield using a transition metal complex as a catalyst, which complex has as a ligand either one selected from the (R, R) and (S, S) forms of the above bisphosphine.

EXAMPLES

The present invention will be further described in greater detail by way of examples. However, the invention should not be construed as being limited to these examples.

Example 1

Synthesis of (−)-(S, S)-1,2-bis[Methyl(1,1,3,3-tetramethybutyl)-phosphino]ethane-rhodium Metal Complex Synthesis of [Methyl(1,1,3,3-tetramethylbutyl) phosphinoyl]-acetate After being evacuated with nitrogen, a 1-liter stainless autoclave was charged at room temperature with 300 ml of n-hexane as a solvent, 112.2 g (1.0 mol) of isobutylenes (a mixture of 2,4,4-trimethyl-1-pentene 75% and 2,4,4-trimethyl-2-pentene 22%) and 34.0 g (1.0 mol) of phosphine. The reaction temperature was elevated to 80° C., and 96.1 g (1.0 mol) of methane sulfonate was added over about 3 hours with a pressure pump. The pressure in the autoclave dropped from 12.5 atm to 4.5 atm. The reaction mixture was further matured for 4 hours with the temperature maintained at 80° C. Upon completion of the reaction, the system was cooled to room temperature, and unreacted phosphine was vented, followed by sufficient evacuation of the system with nitrogen. The reaction product was discharged out of the autoclave, let to stand overnight at room temperature and then separated to remove the methane sulfonate left at a lower phase. The n-hexane phase was vacuum-distilled to give 98.3 g (67.2% yield) of a colorless transparent liquid. The liwuid was found to be 1,1,3,3-tetramethylbutyl phosphine having a boiling point of 79 to 80° C. (62 mmHg). The results of this compound analyzed by NMR and other means are shown below.

$^1$H NMR (δ, CDCl$_3$); 1.02 (s, 9H), 1.32 (d, 6H, J=10.8 Hz), 1.63 (s, 2H), 2.94 (d, 2H, J=190.2 Hz); $^{31}$P NMR (δ, CDCl$_3$); −68.2 (t, J=190.2 Hz); FT-IR (neat, cm$^{-1}$); 2950, 2880, 2275, 1465, 1360, 1065; GC-MS (Pos., m/e); 146 [M]$^+$.

After being sufficiently evacuated with nitrogen, a 1,000-ml four-neck flask was charged at room temperature with 73.1 g (0.5 mol) of the 1,1,3,3-tetramethylbutyl phosphine and 212.9 g (1.5 mol) of methyl iodide. When heated to the reflux temperature, the reaction mixture clouded and deposited crystals, and heating was continued until stirring became difficult to perform. The crystals were filtered after the addition of 300 ml of n-hexane and further washed with hexane. The resultant crystals were dissolved in 300 ml of pure water, and the solution was mixed with 400 ml of hexane as a solvent to be used for extraction to effect. To this mixture, 1.1 mol of aqueous caustic soda was added, followed by separation under a nitrogen atmosphere. The hexane phase was concentrated and then distilled in vacuo to give 63.9 g (79.8% yield) of a colorless transparent liquid. The liquid was found to be (1,1,3,3-tetra-methylbutyl) methyl phosphine having a boiling point of 63 to 66° C. (16 mmHg). The results of this compound analyzed by NMR and other means are shown below.

$^1$H NMR (δ, CDCl$_3$); 0.99 (S, 9H), 1.01 (d, 3H, J=3.1 Hz), 1.20 (d, 6H, J=11.8 Hz), 1.42 (d, 2H, J=9.2 Hz), 3.00 (d, 1H, J=181.7 Hz); $^{31}$P NMR (δ, CDCl$_3$); −33.80 (d, J=181.1 Hz); FT-IR (neat, cm$^{-1}$); 2965, 2280, 1470, 1364, 1296, 1236, 972; GC-MS (Pos., m/e); 160 [M]$^+$.

After being sufficiently evacuated with nitrogen, a 1,000-ml four-nedk flask was charged with 48.0 g (0.3 mol) of the (1,1,3,3-tetramethylbutyl)methyl phosphine and 150 ml of ethanol, and 100.2 g (0.9 mol) of bromoethyl acetate was added dropwise. After the dropwise addition, the reaction mixture was matured for 3 hours at the reflux temperature and concentrated with an evaporator to remove the solvent. Thereafter, 200 ml of pure water was added, and 2.2 mol of aqueous sodium hydroxide was added dropwise at room temperature. This solution was further matured for 3 hours at the reflux temperature. Extraction was effected twice with dichloromethane, and the resultant organic phase was washed with a 0.1 N aqueous solution of hydrochloric acid and then with pure water. The organic phase was dewatered over sodium sulfate anhydride and let to stand overnight, followed by filtration and subsequent concentration with an evaporator, whereby a white solid was obtained. The solid was purified by recrystallization with acetone to give 17.1 g (24.3% yield) of white crystals having a melting point of 99 to 100° C. Analysis revealed that the crystals were [methyl (1,1,3,3-tetramethylbutyl)phosphinoyl]acetate. The results of this compound analyzed by NMR and other means are shown below.

$^1$H NMR (ppm, CDCl$_3$); 1.06 (s, 9H), 1.34 (d, 6H, J=17.9 Hz), 1.52 (d, 2H, J=8.8 Hz), 1.71 (d, 3H, J=12.3 Hz), 2.71 (dd, 1H, J=9.2 Hz, J=13.4 Hz), 3.00 (dd, 1H, J=14.3 Hz, J=13.4 Hz), 10.78 (s, 1H); FAB-MASS (Pos.); m/z=235 [M$^+$H$^+$]; FT-IR (KBr, cm$^{-1}$); 2955, 2872, 1714, 1270, 1158, 1103, 970, 896;

Optical Resolution of ([Methyl(1,1,3,3-tetramethylbutyl)-phosphinoyl]acetate)

In a 300-ml flask, 16.7 g (71.5 mmol) of the resultant [methyl(1,1,3,3-tetramethylbutyl)phosphinoyl]acetate and 200 ml of methyl ethyl ketone were placed, and 8.7 g (71.5 mmol) of (-)-(S)-1-phenylethylamine was added. The mixture was let to stand overnight at room temperature to deposit crystals, and filtration and vacuum drying gave 20.5 g of white crystals. Subsequently, the crystals were recrystallized twice with 220 ml of acetone to give 2.6 g of white crystals which were then liberated with hydrochloric acid and extracted with dichloromethane, whereby 1.2 g of white crystals were obtained. The resultant crystals were found to be (-)-(S)-[methyl(1,1,3,3-tetramethylbutyl)phosphinoyl]-acetate having a melting point of 99 to 100° C., an optical purity of 98.6% ee and an optical rotation of [α] 25D=-15.8 (C 1.04, CHCl$_3$). The results of this compound analyzed by NMR and other means are shown below.

$^1$H NMR (ppm, CDCl$_3$); 1.06 (s, 9H), 1.34 (d, 6H, J=18.0 Hz), 1.53 (d, 2H, J=8.7 Hz), 1.69 (d, 3H, J=12.0 Hz), 2.71 (dd, 1H, J=9.6 Hz, J=13.2 Hz), 3.04 (dd, 1H, J=15.3 Hz, J=13.2 Hz), 11.32 (s, 1H); FAB-MASS (Pos.); m/z=235 [M$^+$H$^+$].

Synthesis of 1,2-bis[Methyl(1,1,3,3-tetramethylbutyl)-phosphinoyl]ethane

In a 50-ml cylindrical glass container, 0.95 g (0.004 mol) of the (-)-(S)-[methyl(1,1,3,3-tetramethylbutyl) phosphinoyl]acetate having an optical rotation of [α] 25D=-15.8 (C 1.0$_4$, CHCl$_3$), an optical purity of 98.6% ee and a melting point of 99 to 100° C. was dissolved in 30 ml of methanol, and to the solution was added 0.02 g of sodium methoxide as an electrolyte. Platinum electrodes (2 cm×4 cm×1 mm) were disposed at an electrode-to-electrode distance of 1 mm, and constant-dc electrolysis was carried out at 0.7 A. The reaction mixture was cooled with ice water to maintain the temperature substantially constant and stirred to make the same homogeneous. After power distribution was performed for 3 hours, the reaction liquid was analyzed by high-speed liquid chromatography to find that the starting material was decreased by 98.7%.

The solvent was removed by distillation using an evaporator, and the unreacted starting material was dissolved in 100 ml of dichloromethane and extracted with a 1 N aqueous solution of sodium hydroxide, followed by washing of the organic phase with pure water. This phase was dehydrated overnight with sodium sulfate anhydride, and the solvent was removed with an evaporator, whereby 0.54 g of white crystals was obtained (crude yield: 70.4%). The crystals were further purified by recrystallization with acetone to give 0.47 g of white crystals having a melting point of 117 to 119° C. (crystallization yield: 61.0%).

The resultant product was found to be (-)-(S, S)-1,2-bis-[methyl(1,1,3,3-tetramethylbutyl)phosphinoyl]ethane having an optical rotation of [α] 25D=-2.85 (C 1.05, CHCl$_3$). The results of this compound analyzed by NMR and other means are shown below.

FAB-MS (Pos.); 379 [M$^+$H]$^+$; $^1$H NMR (ppm, CDCl$_3$); 1.06 (s, 18H), 1.31–1.41 (m, 18H), 1.49–1.62 (m, 4H), 1.70–1.81 (m, 2H), 2.17–2.29 (m, 2H).

(Synthesis of (-)-(S, S)-1,2-bis[Methyl(1,1,3,3-tetramethylbutyl)-phosphino]ethane In a 30-ml eggplant-shaped flask, 0.4 g (0.001 mol) of the (-)-(S, S)-1,2-bis[methyl(1,1,3,3-tetramethylbutyl) phosphinoyl]ethane and 5 ml of phenylsilane were placed, and the mixture was reacted at 120° C. for 12 hours under a nitrogen stream. On cooling, excess phenylsilane was removed in vacuo, and 3 ml of a deaerated solvent was added, which solvent was composed of ethanol water (10:1) and having 0.56 g (10 mmol) of potassium hydroxide dissolved. Extraction was then performed three times with 5 ml of deaerated ether. The ether phase was dehydrated over sodium sulfate anhydride, and the solvent was removed in vacuo, whereby 0.35 g of an oily product was obtained. The results of this compound analyzed by NMR are shown below.

$^-$P NMR (δ, CDCl$_3$); –4.53 (s)

Synthesis of Rhodium Complex

This (-)-(S, S)-1,2-bis[methyl(1,1,3,3-tetramethylbutyl)-phosphino]ethane) in an amount of 0.35 g (0.001 mol) was dissolved in dehydrated THF under a nitrogen stream, and the solution was mixed under a nitrogen atmosphere with a dehydrated THF slurry containing 0.37 g (0.001 mol) of [Rh(nbd)$_2$]BF$_4$. Immediately after the mixing, the liquid turned uniformly orange. Removal of most of THF in vacuo and addition of hexane deposited orange crystals. The quantity was 0.56 g and the yield 88.8%.

Example 2

Synthesis of (+)-(R, R)-1,2-bis[Methyl(1,1,3,3-tetramethylbutyl)-phosphino]ethane-rhodium Metal Complex A mother liquid abundant in (+)-(R)-[methyl(1,1,3,3-tetramethybutyl)phosphinoyl]acetate, i.e., a mother liquid left after separating the (-)-(S)-[methyl(1,1,3,3-tetramethybutyl)-phosphinoyl]acetate in Example 1, was let to stand overnight at room temperature to deposit crystals.

The crystals were collected by filtration and dried in vacuo so that 2.6 g of white crystals was obtained. The white crystals were further recrystallized with 100 ml of acetone to give 1.5 g of white crystals which were then liberated with hydrochloric acid and extracted with dichloromethane, whereby 1.5 g of white crystals was obtained. The resultant crystals were found to be (+)-(R)-[methyl(1,1,3,3-tetramethylbutyl)phosphinoyl]acetate having a melting point of 98 to 99° C., an optical purity of 93.7% ee and an optical rotation of [α] 25D=+14.8 (C 1.28, CHCl$_3$). The results of this compound analyzed by NMR and other means are shown below.

$^1$H NMR (ppm, CDCl$_3$); 1.06 (s, 9H, CH$_3$), 1.35 (d, 6H, JPCCH=17.9 Hz, CH$_3$), 1.56 (d, 2H, CH$_2$, JPCCH=8.3 Hz), 1.67 (d, 3H, P—CH$_3$, JPCH=10.9 Hz), 2.84 (dd, 1H, JPCH= 9.2 Hz, Jgem=13.4 Hz, P—CH—), 3.02 (dd, 1H, J=14.3 Hz, Jgem=13.4 Hz, P—CH'—), 10.36 (s, 1H, COOH); FAB-MASS (Pos.); m/z=235 [M$^+$H$^+$].

Synthesis of 1,2-bis[Methyl(1,1,3,3-tetramethylbutyl)-phosphinoyl]ethane

In a 50-ml cylindrical glass container, 1.00 g (0.0042 mol) of the (+)-(R)-[methyl(1,1,3,3-tetramethylbutyl)

phosphinoyl]acetate having an optical rotation of [α] 25D=+ 14.8 (C 1.28, CHCl$_3$), an optical purity of 93.7% ee and a melting point of 98 to 99° C. was dissolved in 30 ml of methanol, and to the solution was added 0.02 g of sodium methoxide as an electrolyte. Platinum electrodes (2 cm×4 cm×1 mm) were disposed at an electrode-to-electrode distance of 1 mm, and constant-dc electrolysis was carried out at 0.7 A. The reaction mixture was cooled with ice water to maintain the temperature substantially constant and stirred to homogenize the mixture. Power distribution was performed for 3 hours.

The solvent was removed by distillation using an evaporator, and the unreacted starting material was dissolved in 100 ml of dichloromethane and extracted with a 1N aqueous solution of sodium hydroxide, followed by washing of the organic phase with pure water. This phase was dehydrated overnight with sodium sulfate anhydride, and the solvent was removed with an evaporator, whereby 0.57 g of white crystals was obtained (crude yield: 70.4%). The crystals were further purified by recrystallization with acetone to give 0.47 g of white crystals having a melting point of 118 to 119° C. (crystallization yield: 59.0%).

The resultant product was found to be (+)-(R, R)-1,2-bis-[methyl(1,1,3,3-tetramethylbutyl)phosphinoyl]ethane having an optical rotation of [α] 25D=+2.36 (C 1.04, CHCl$_3$). The results of this compound analyzed by NMR and other means are shown below.

FAB-MS (Pos.); 379 [M$^+$H]$^+$; $^1$H NMR (ppm, CDCl$_3$); 1.06 (s, 18H), 1.31–1.41 (m, 18H), 1.49–1.62 (m, 4H), 1.70–1.81 (m, 2H), 2.17–2.29 (m, 2H);

Synthesis of (+)-(R, R)-1,2-bis[Methyl(1,1,3,3-tetramethylbutyl)-phosphino]ethane In a 30-ml eggplant-shaped flask, 0.4 g (0.001 mol) of the (+)-(R, R)-1,2-bis[methyl(1,1,3,3-tetramethylbutyl) phosphinoyl]-ethane and 5 ml of phenylsilane were placed, and the mixture was reacted at 120° C. for 12 hours under a nitrogen stream. On cooling, excess phenylsilane was removed in vacuo, and 3 ml of a deaerated solvent was added, which solvent was composed of ethanol:water (10:1) and having 0.56 g (10 mmol) of potassium hydroxide dissolved. Extraction was then performed three times with 5 ml of deaerated ether. The ether phase was dehydrated over sodium sulfate anhydride, and the solvent was removed in vacuo, whereby 0.35 g of an oily product was obtained. The results of this compound analyzed by NMR are shown below.

$^{31}$P NMR (δ, CDCl$_3$): −4.53 (s)

Synthesis of Rhodium Complex

This (+)-(R, R)-1,2-bis[methyl(1,1,3,3-tetramethylbutyl)-phosphino]ethane) in an amount of 0.35 g (0.001 mol) was dissolved in dehydrated THF under a nitrogen stream, and the solution was mixed under a nitrogen atmosphere with a dehydrated THF slurry containing 0.37 g (0.001 mol) of [Rh(nbd)$_2$]BF$_4$. Immediately after the mixing, the liquid turned uniformly orange. After removal of most of THF in vacuo and addition of hexane orange crystals were deposited. The quantity was 0.55 g and the yield 84.2%.

Asymmetric Hydrogenation

Example 3

A 100-ml glass autoclave was charged with 143.1 mg (1.0 mmol) of a methyl ester of 2-acetamide acrylate and 1.3 mg (0.002 mmol) of the rhodium complex obtained in Example 1, and the system was evacuated three times with nitrogen. Then, 5 ml of dehydrated methanol was added while the system was being cooled with ice water, and hydrogen gas was blown under pressure into the system up to 2 atm. Stirring was conducted at room temperature for 70 minutes. The reaction liquid was discharged out of the autoclave and analyzed using an optically active column (Chrome Pack, Chiral-L-Val, 25 m×0.25 mm ID, 120° C.). It was confirmed that a hydrogenated product, i.e., a (R)-N-acetylalanine methyl ester, had been obtained with an optical purity of 96.3% ee.

Example 4

The same reaction as in Example 3 was run except that the rhodium complex catalyst was changed to that obtained in Example 2. It was confirmed that a hydrogenated product, i.e., a (S)-N-acetylalanine methyl ester, had been obtained with an optical purity of 97.3% ee.

Example 5

The same reaction as in Example 3 was run except that 205.2 mg (1.0 mmol) of α-acetamide cinnamate was used in place of the methyl ester. The reaction liquid was discharged out of the autoclave and methyl-esterified by adding 1 ml of trimethylsilyl diazomethane and by stirring the reaction mixture at room temperature for 30 minutes. The ester was analyzed using an optically active HPLC column (Chiral Cell OD-H, 10 ml/minute, 10% 2-isopropanol/hexane). It was confirmed that a hydrogenated product, i.e., a (R)-N-acetylalanine methyl ester, had been obtained with an optical purity of 95.9% ee.

Example 6

The same reaction as in Example 4 was run except that the rhodium complex catalyst was changed to that obtained in Example 2. It was confirmed that a hydrogenated product, i.e., a (S)-N-acetylalanine methyl ester, had been obtained with an optical purity of 96.4% ee.

Industrial Applicability

The present invention provides a rhodium complex having as a ligand 1,2-bis[methyl(1,1,3,3-tetramethybutyl) phosphinoyl]-ethane. The rhodium complex of the invention is useful as a catalyst for asymmetric hydrogenation and is capable of achieving both forms of (R, R) and (S, S) as absolute configurations. Hence, this rhodium complex permits, with good efficiency and high selectivity, amino acids and the like to be produced to have a (S)-form absolute configuration as well as a (R)-form absolute configuration. Furthermore, the alkyl group in the phosphine compound of the invention has 8 carbon atoms and exhibits properties markedly resembling a lipophilic group. Nothing is known about a phosphine ligand structured to contain this specific type of alkyl group, and asymmetric hydrogenation is possible which is characteristic with respect to a substrate used.

What is claimed is:

1. A 1,2-bis(methyl(1,1,3,3-tetramethylbutyl)phosphino)-ethane represented by the following general formula (1):

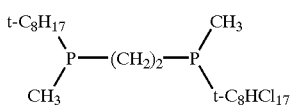

(1)

(where t—$C_8H_{17}$ denotes 1,1,3,3-tetramethylbutyl).

2. An optically active form of the 1,2-bis(methyl(1,1,3,3-tetramethylbutyl)phosphino)ethane represented by the general formula (1) according to claim 1.

3. A process for producing a 1,2-bis(methyl(1,1,3,3-tetramethylbutyl)phosphino)ethane according to claim 1 or 2, comprising: subjecting a phosphine oxide carboxylate represented by the following general formula (2):

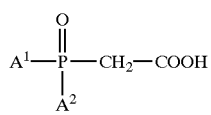

(2)

(where $A^1$ and $A^2$ denote a methyl group and 1,1,3,3-tetramethyl-butyl group, respectively) to Kolbe' electrolytic coupling reaction, thereby obtaining a 1,2-bis(methyl(1,1,3,3-tetramethylbutyl)phosphinoyl)-ethane represented by the following general formula (3):

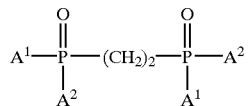

(3)

(where $A^1$ and $A^2$ have the same meanings as defined above); and then reducing the resultant 1,2-bis(methyl(1,1,3,3-tetramethylbutyl)phosphinoyl)-ethane with a reducing agent.

4. A process for producing an optically active form of the 1,2-bis(methyl(1,1,3,3-tetramethylbutyl)phosphino)ethane according to claim 3, wherein an optically active form of the phosphine oxide carboxylate is subjected to the Kolbe' electrolytic coupling reaction.

5. A transition metal complex comprising as a ligand a 1,2-bis(methyl(1,1,3,3-tetramethylbutyl)phosphino)ethane or an optically active form thereof represented by the general formula (1) according to claim 1 or 2.

6. A process for producing a saturated carboxylic acid or an ester thereof represented by the following general formula (5):

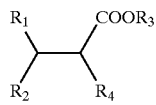

(5)

(where $R^1$, $R^2$ and $R^3$ denote a hydrogen atom, a straight- or branched-alkyl, aryl or aralkyl group, and $R^4$ denotes a straight- or branched-alkyl, aryl, aralkyl, —$CH_2COOR^5$ (where $R^5$ denotes a straight- or branched-alkyl, aryl or aralkyl group) or —$NHR^6$ group (where $R^6$ denotes a formyl straight- or branched-alkyl, aryl or aralkyl group), which process comprises hydrogenating asymmetrically an unsaturated carboxylic acid or an ester thereof represented by the following general formula (4):

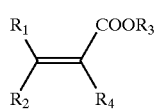

(4)

(where $R^1$, $R^2$, $R^3$ and $R^4$ have the same meanings as defined above), using as a catalyst the transition metal complex according to claim 5.

7. A process for producing a saturated carboxylic acid or an ester thereof according to claim 6, wherein the transition metal complex for use as a catalyst is a rhodium metal complex or an ester thereof.

* * * * *